United States Patent
Palti et al.

(10) Patent No.: US 11,255,841 B2
(45) Date of Patent: Feb. 22, 2022

(54) DISTRIBUTED FLUID-FLOW SYSTEMS WITH EQUALIZED FLOW RATE

(71) Applicant: Yoram Palti, Haifa (IL)

(72) Inventors: Yoram Palti, Haifa (IL); Matan Dishon, Kibbutz Mizra (IL)

(73) Assignee: Nano2cure Ltd., Haifa (IL)

( * ) Notice: Subject to any disclaimer, the term of this patent is extended or adjusted under 35 U.S.C. 154(b) by 257 days.

(21) Appl. No.: 16/529,262

(22) Filed: Aug. 1, 2019

(65) Prior Publication Data

US 2020/0041486 A1 Feb. 6, 2020

Related U.S. Application Data

(60) Provisional application No. 62/714,353, filed on Aug. 3, 2018.

(51) Int. Cl.
*G01N 33/50* (2006.01)
*B01L 3/00* (2006.01)

(52) U.S. Cl.
CPC ............ *G01N 33/50* (2013.01); *B01L 3/5027* (2013.01); *B01L 2300/0877* (2013.01); *B01L 2400/0487* (2013.01)

(58) Field of Classification Search
CPC ................... G01N 33/50; B01L 3/5027; B01L 2300/0877; B01L 2400/0487
See application file for complete search history.

(56) References Cited

U.S. PATENT DOCUMENTS

| 9,138,522 | B2 | 9/2015 | Palti |
| 9,827,534 | B2 | 11/2017 | Palti |
| 2014/0065597 | A1 | 3/2014 | Vulto et al. |
| 2015/0024374 | A1* | 1/2015 | Palti ...................... B01D 69/04 435/2 |

FOREIGN PATENT DOCUMENTS

WO 2009155248 A1 12/2009

OTHER PUBLICATIONS

Li et al., "Transfer of vertically aligned carbon nanotube arrays onto flexible substrates for gecko-inspired dry adhesive application," RSC Advances, Issue 58, May 2015 (Abstract).
Partial International Search Report and Provisional Written Opinion issued in application No. PCT/IB2019/056585, dated Jan. 8, 2020.
Ping et al., "Vertically aligned carbon nanotube arrays as a thermal interface material," APL Mater, vol. 7, Feb. 9, 2002, Feb. 2019.
Strobl et al., "c-VACNT (TM) enabled Fluid Reactor Innovations: a NanotoMacro (TM) transformation," CVD Equipment Corporation, poster, Jun. 2019.

* cited by examiner

*Primary Examiner* — Jennifer Wecker
*Assistant Examiner* — Kathryn Elizabeth Limbaugh
(74) *Attorney, Agent, or Firm* — Potomac Law Group, PLLC

(57) ABSTRACT

Distributed liquid-flow systems—in which flow spreads out from a system inlet and traverses the system through multiple discrete, smaller flow channels—are constructed to minimize variations in flow-resistance-induced pressure drop from the system inlet to entrances to the flow channels. Because flow-driving pressure will be more uniform at the entrances to the flow channels, flow along the channels will be more uniform. Disclosed embodiments may be particularly suitable or advantageous for use in gas-exchange/artificial lung devices.

13 Claims, 8 Drawing Sheets

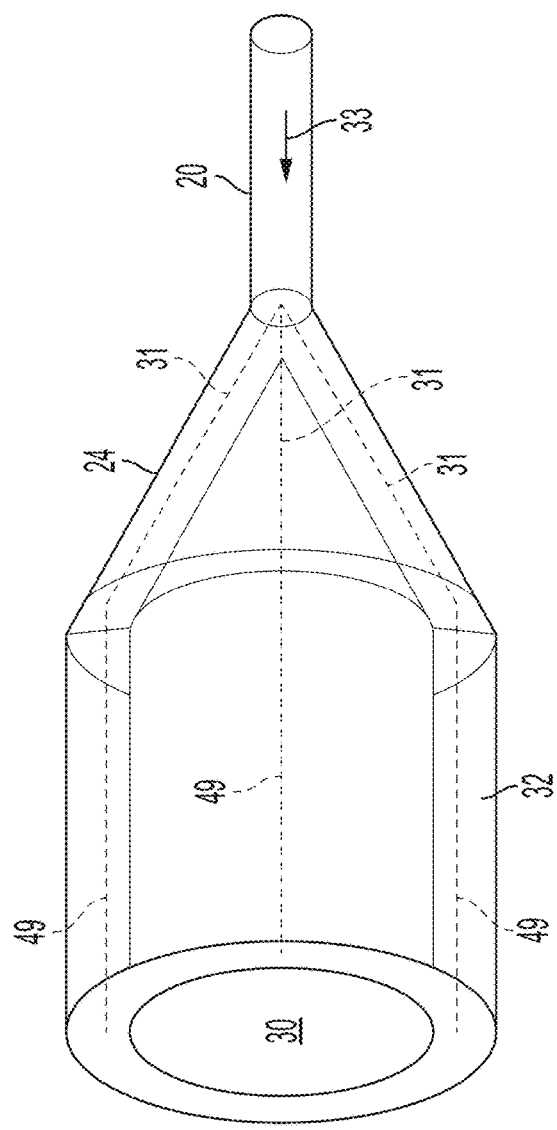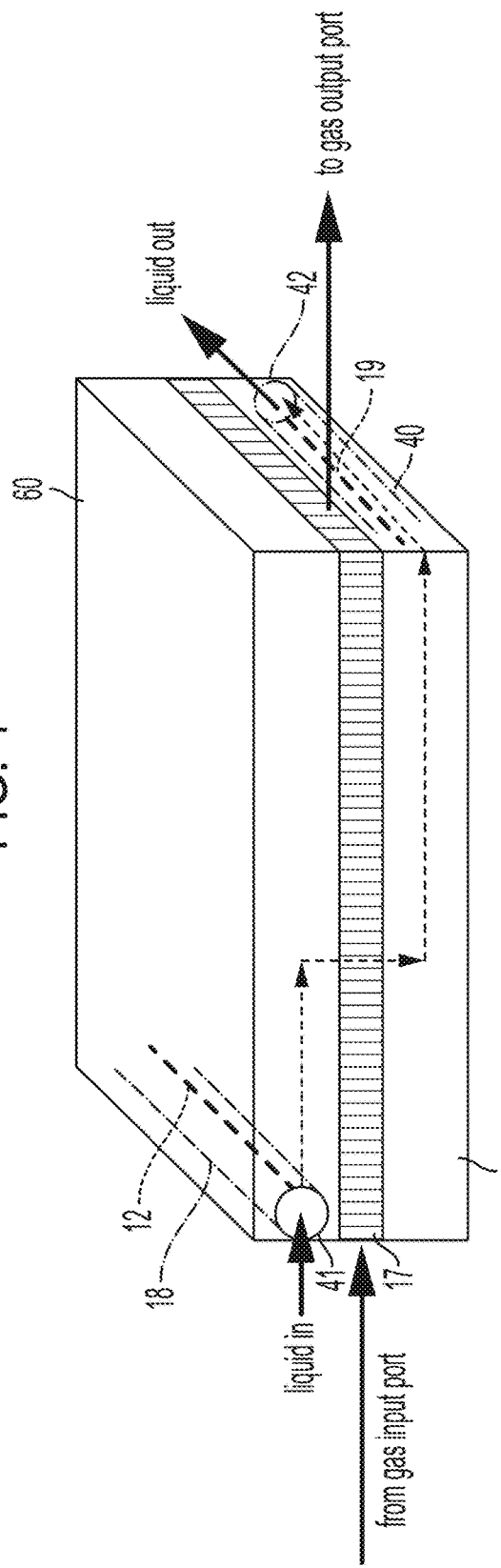
FIG. 4
FIG. 5

DISTRIBUTED FLUID-FLOW SYSTEMS WITH EQUALIZED FLOW RATE

CROSS REFERENCE TO RELATED APPLICATIONS

This application claims the benefit of U.S. Provisional Application 62/714,353 filed Aug. 3, 2018, which is incorporated herein by reference in its entirety.

FIELD OF THE INVENTION

This application is directed to fluid-flow systems in which liquid flows in a distributed manner, i.e. through a large number of channels, to pass from an upstream location to a downstream location.

BACKGROUND

In certain systems (including but not limited to systems that exchange molecules between a liquid and a gas), an amount of liquid flowing from one location to another is distributed among a large number of discrete liquid flow channels.

FIG. 1 depicts a prior art gas exchange system in which flow proceeds from right to left. The system includes a plurality of uniform flow channels 9 where gas exchange occurs (i.e. exchange of molecules between the liquid within the flow channel 9 and gas that surrounds the flow channel 9). The total flow pathway for any given flow channel includes a first portion through the system inlet 20, a second expanding portion 21 between the system inlet 20 and the inlet of each of the flow channels 9, as well as a third portion through each of the channels 9 itself.

With such an arrangement, the length of the portion of flow pathway from the system inlet 20 to the inlet of a given channel 9 will vary depending on the position of the channel. Thus, the entrances to centrally located channels 9 will be closer to the system inlet 20 than the entrances to more off-axis channels 9. As a result, flow pathway 1 is longer than flow pathway 2 and, assuming a uniform width of the second portion 21 (in the case of a flat or planar flow-distributing arrangement), the resistance to flow along a given flow pathway will vary accordingly. For example, there will be greater total resistance along flow pathway 1 than along flow pathway 2. As a result, even if all the flow channels 9 have identical dimensions and identical flow resistances, liquid will not enter the various channels 9 uniformly, and the velocity of liquid along each of the various channels 9—and hence the efficacy of processes (such as material transport by flow or gas exchange) occurring along the length of a given channel 9—will vary from channel to channel When the variation between the flow rate in the slowest channel and the fastest channel gets too large, problems can result. More specifically, if the dwell time in a given channel is too short, there will not be enough time for effective gas exchange to occur. On the other hand, if the dwell time in a given channel is too long, it will reduce the overall capacity of the system. In addition, during initial filling of the system, if some channels have flow resistances that are significantly higher than other channels, those high resistance channels may never fill in with fluid, thereby reducing the overall capacity of the system. Finally, in situations where the fluid passing through the channels 9 is blood, there is a risk of coagulation whenever the rate of flow in any given channel is too slow.

SUMMARY OF THE INVENTION

One aspect of the invention is directed to a first distributed-flow liquid flow system. The first system comprises a gas-exchange plate having an upstream side and a downstream side. The plate has a transit region that includes at least 1000 liquid-flow channels extending through the plate in a first direction from the upstream side of the plate to the downstream side of the plate. The transit region has a length and a width, and the plate is configured so that a gas can permeate portions of the plate that are outside the liquid-flow channels. The first system also comprises a distribution pool plenum located on the upstream side of the plate adjacent to the transit region. The distribution pool plenum is shaped and dimensioned to convey the liquid to the entire upstream side of the transit region, and the distribution pool plenum is at least as wide as the transit region. The first system also comprises a collection pool plenum located on the downstream side of the plate adjacent to the transit region. The collection pool plenum is shaped and dimensioned to receive liquid that has transited the transit region, and the distribution pool plenum is at least as wide as the transit region. The first system also comprises a liquid distribution channel located upstream of the distribution pool plenum. The liquid distribution channel has an elongated liquid delivery opening that extends across the width direction of the transit region, and the liquid delivery opening is positioned to deliver liquid to the distribution pool plenum. The first system also comprises a liquid collection channel located downstream of the collection pool plenum. The liquid collection channel has an elongated liquid collection opening that extends across the width direction of the transit region, and the liquid collection opening is positioned to receive liquid from the collection pool plenum. The first system also comprises a liquid input port disposed in fluid communication with the liquid distribution channel; a liquid output port disposed in fluid communication with the liquid collection channel; and at least one gas port disposed in fluid communication with the portions of the plate that are outside the liquid-flow channels.

In some embodiments of the first system, the liquid distribution channel is positioned sufficiently upstream of the distribution pool plenum to form a distribution pool plenum feeder portion extending from the liquid delivery opening to a leading edge of the distribution pool plenum, over which feeder portion the flow of liquid exiting from the liquid delivery opening becomes essentially uniform before entering the distribution pool plenum.

In some embodiments of the first system, the liquid collection channel is positioned sufficiently downstream of the collection pool plenum to form a collection pool plenum run-out portion extending from a trailing edge of the collection pool plenum to the liquid collection opening so as to maintain essentially uniform flow of liquid as it exits the collection pool plenum.

In some embodiments of the first system, the liquid delivery opening has a width that varies along the length of the liquid distribution channel, from a liquid entry location to a distal end, so as to maintain uniform velocity of liquid exiting the liquid distribution channel along the length of the liquid distribution channel.

In some embodiments of the first system, the liquid collection opening has a width that varies along the length of the liquid collection channel, from a distal end to a liquid exit location, so as to maintain uniform velocity of liquid entering the liquid collection channel along the length of the liquid collection channel.

In some embodiments of the first system, the liquid distribution channel has a liquid inlet and the liquid collection channel has a liquid outlet and the liquid inlet and liquid outlet are located on opposite sides of the transit region in both widthwise and lengthwise directions.

In some embodiments of the first system, the liquid is blood and the gas comprises air. In some embodiments of the first system, the liquid is blood and the gas comprises oxygen.

In some embodiments of the first system, the plate comprises a field of at least one million vertically oriented nanotubes, and the liquid-flow channels comprise vertical voids within the fields, the voids having diameters between 2 and 500 μm. The vertically oriented nanotubes are positioned close enough together to retain the liquid within the voids, and the vertically oriented nanotubes are positioned far enough apart so that gas can reach the liquid-flow channels.

In some embodiments of the first system, the at least one gas port comprises an input gas port configured to supply the gas to the portions of the plate that are outside the liquid-flow channels, and an output gas port configured to vent the gas from the portions of the plate that are outside the liquid-flow channels.

In some embodiments of the first system, the distribution pool plenum has a constant height. Optionally, in these embodiments, the collection pool plenum may have a constant height.

In some embodiments of the first system, the distribution pool plenum has a sloped roof.

Another aspect of the invention is directed to a second distributed-flow liquid-flow system. The second system comprises a system inlet, a system outlet, and a plurality of liquid-flow channels. These liquid-flow channels are arranged to convey liquid flowing along a plurality of flow pathways extending from the system inlet to the system outlet, with each of the liquid-flow channels having a length that is essentially identical, a flow resistance that is essentially identical, a channel inlet, and a channel outlet. The channel inlets are spaced from the system inlet and arranged in a distributed configuration relative to the system inlet. The liquid-flow channels are arranged with their inlets all at essentially the same distance from the system inlet such that flow-resistance from the system inlet to the channel inlets, and hence flow, is essentially uniform across the space between the system inlet and the channel inlets.

In some embodiments of the second system, the liquid-flow channels are arranged parallel to each other with the channel inlets all being located along a curve of constant radius centered at the system inlet so as to be located at essentially the same distance from the system inlet. In these embodiments, the liquid-flow channels may all lie within a plane containing the system inlet and the curve of constant radius is an arc lying within the plane. Alternatively, in these embodiments, the liquid-flow channels may lie within a three-dimensional cylindrical region and the curve of constant radius is a curved surface defined by the cap portion of a spherical sector.

Another aspect of the invention is directed to a third distributed-flow liquid flow system. The third system comprises a system inlet, a system outlet, and a plurality of liquid-flow channels. These liquid-flow channels are arranged to convey liquid flowing along a plurality of flow pathways extending from the system inlet to the system outlet, with each of the liquid-flow channels having a length that is essentially identical, a flow resistance that is essentially identical, a channel inlet, and a channel outlet. The channel inlets are spaced from the system inlet and arranged in a distributed configuration relative to the system inlet. The liquid-flow channels are arranged parallel to each other and extend in a liquid-flow direction and a line passing through the system inlet and extending in the liquid-flow direction defines a flow axis. The channel inlets of liquid-flow channels that lie progressively farther away from the flow axis are located progressively closer to the system inlet so as to compensate for increased flow-resistance and pressure drop associated with flow that is located closer to a system boundary than more central, free-stream flow is located, thereby maintaining essentially uniform flow resistance, and hence flow, across the space between the system inlet and the channel inlets.

In some embodiments of the third system, the liquid-flow channels all lie within a plane. Optionally, in these embodiments, the inlets to the liquid-flow channels on each side of the flow axis are aligned with each other.

In some embodiments of the third system, the liquid-flow channels lie within a cylindrical region. Optionally, in these embodiments, the inlets to the liquid-flow channels all lie along a conical surface.

BRIEF DESCRIPTION OF THE DRAWINGS

FIG. 4 is a schematic diagram illustrating a third embodiment of a multi-channel, distributed liquid-flow system.

FIG. 5 is a perspective schematic diagram of a fourth embodiment of a multi-channel, distributed liquid-flow system.

DESCRIPTION OF THE PREFERRED EMBODIMENTS

Embodiments of distributed liquid-flow systems as disclosed herein may have particular utility in connection with gas-exchange/artificial lung units, including but not limited to the systems disclosed in U.S. Pat. Nos. 9,138,522 and 9,827,534, which are incorporated herein by reference. Those patents disclose systems in which flow-channels along which respiratory gas-exchange takes place are formed as voids within fields of densely packed carbon nanotubes.

Figure 2:
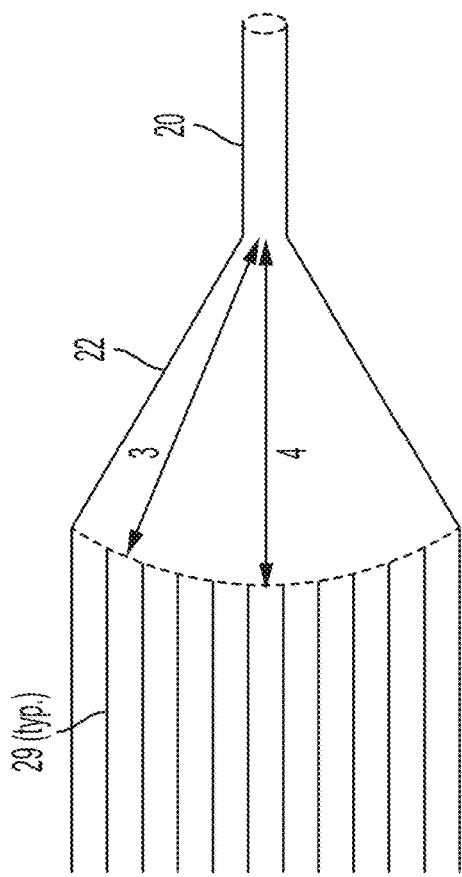
FIG. 2 is a schematic diagram illustrating a first embodiment of a multi-channel, distributed liquid-flow system.

FIG. 2 depicts a first embodiment of a distributed-flow liquid-flow system that reduces the variations in flow rate through the various channels of the system. Flow proceeds from right to left. This embodiment includes a plurality of liquid-flow channels 29, each of which has the same length and flow resistance. Gas exchange occurs in these liquid-flow channels 29 (i.e. exchange of molecules between the liquid within the flow channel 29 and gas that surrounds the flow channel 29). In this embodiment, the various liquid-flow channels 29 are arranged parallel to each other, with their respective inlets located along a curve of constant radius, e.g., an arc that is centered at the left side of the system inlet 20. This positions the openings to all liquid-flow channels 29 at the same distance from a system inlet, so that as the liquid fans out through fan-shaped flow-dispersion region 22 and enters the various flow channels, the flow has to traverse the same distance irrespective of the position of the inlet to any given channel. The outlets of each of the liquid-flow channels 29 empty into a common collection pool.

Figure 1:
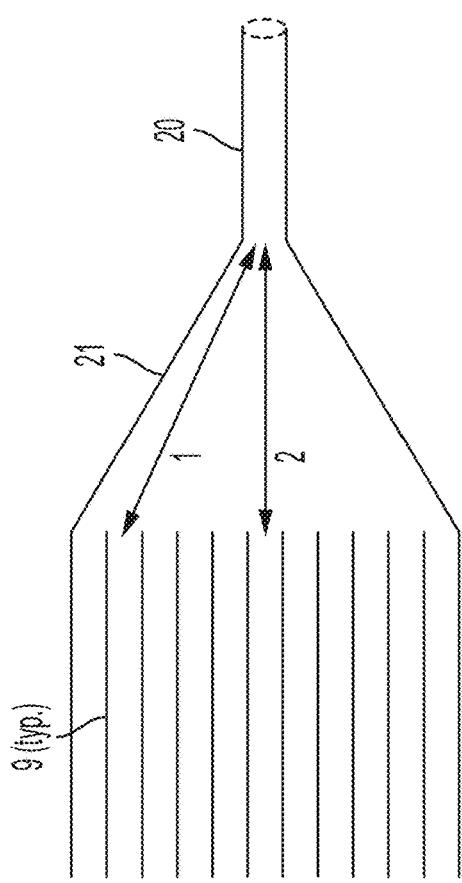
FIG. 1 is a schematic diagram illustrating variation in length, with position, of the flow pathways in a multi-channel, distributed liquid-flow system according to the prior art.

Thus, in this embodiment, the length of flow pathway 3 from the system inlet 20 to the entrance of one of the liquid-flow channels 29 will be essentially the same as the length of flow pathway 4 from the system inlet 20 to the entrance of any other flow channel 29 in the system. Therefore, assuming a constant width (in the direction into and out of the plane of the page) of the fan-shaped flow-dispersion region 22, total flow resistance along any given flow pathway from the system inlet 20 into any given one of the liquid-flow channels 29 will be more uniform than it was in the case of FIG. 1. As a result, pressure drop along any given flow pathway will be more uniform, such that the flow-driving pressure head at the entrance to all liquid-flow channels 29 will be more uniform. This, in turn, leads to more uniform flow into and along the liquid-flow channels 29, thus reducing the variations among all liquid-flow channels 29.

The configuration illustrated in FIG. 2 is planar. However, the same constant-length concept could also be implemented in a three-dimensional configuration. In that case, the curve of constant radius along which the inlets of the flow channels lie would be defined by the cap portion of a spherical sector.

Figure 3:
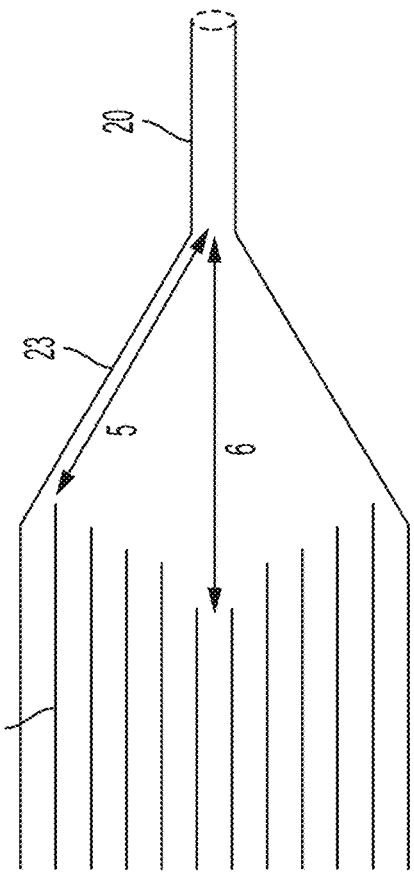
FIG. 3 is a schematic diagram illustrating a second embodiment of a multi-channel, distributed liquid-flow system.

FIG. 3 depicts another embodiment of a distributed-flow liquid-flow system that reduces the variations in flow rate through the various channels of the system. Gas exchange occurs in liquid-flow channels 39 (i.e. exchange of molecules between the liquid within the flow channel 39 and gas that surrounds the flow channel 39). Flow proceeds from right to left. In this embodiment, the various liquid-flow channels 39 are arranged parallel to each other and each of the liquid-flow channels 39 has the same diameter and length and thus flow resistance and empties into a common collection pool, as in the embodiment described above in connection with FIG. 2. However, in this FIG. 3 embodiment, the lengths of the flow pathways from the system inlet 20 to the entrances to the various liquid-flow channels 39 vary depending on the position of the channels.

In particular, flow pathways to channels 39 that lie farther away from the central flow axis of the system (i.e., a line extending through the system inlet 20 and parallel to the liquid-flow channels 39) are shorter than flow pathways to channels 39 that are more centrally located, i.e., that lie closer to the central flow axis of the system. Thus, for example, the length of flow pathway 5, which extends along and close to the peripheral wall of the flow-dispersion region 23, is less than the length of flow pathway 6, which passes through the center of the flow-dispersion region 23 where flow is more free-stream in nature.

This variation in length of the flow pathways is preferably configured to at least partially compensate for the greater drag due to friction as the liquid flows along the peripheral walls of the flow-dispersion regions 23, which results in a parabolic, boundary-layer velocity profile. By increasing the lengths of the more central flow pathways relative to the lengths of the flow pathways to the more off-axis channels 39, total drag—and therefore pressure drop—experienced along the central flow pathways is increased relative to what it would be if all flow pathways were of equal length. As a result, liquid enters the various liquid-flow channels 39 at a more uniform pressure, so that flow along all channels 39 will be more uniform.

As will be understood by persons skilled in the art, the geometric nature of the particular displacement of the channel inlets will depend on the viscosity of the liquid for which the system is designed, the wall properties, etc. Furthermore, the configuration illustrated in FIG. 3 is planar. However, the same resistance-compensating variation of flow length concept could also be implemented in a 3D configuration by varying the shape of the 3D surface that includes all of the channel inlets. For example, the 3D surface that includes all of the channel inlets could have a conical shape.

FIG. 4 depicts another embodiment that is configured to reduce the variations in flow rate through the various channels of the system. Flow 33 proceeds from right to left. A plurality of identical liquid-flow channels 49 are distributed throughout the walls of a hollow cylindrical section 32 of the system. Gas exchange occurs in these liquid-flow channels 49 (i.e. exchange of molecules between the liquid within the flow channel 49 and gas that surrounds the flow channel 49). Note that while only three liquid-flow channels 49 are explicitly illustrated in FIG. 4 for clarity, practical systems will have a much larger number (e.g., thousands or hundreds of thousands) of liquid-flow channels 49. The liquid-flow channels 49 are arranged parallel to each other and radially spaced from the central axis of rotational symmetry of the system. In alternative embodiments (not shown), the channel-bearing section may be formed as a solid cylinder, so long as all of the flow channels are disposed near the periphery of the cylinder, and the central portion of the cross-sectional area of the solid cylinder does not contain any flow channels, so as to correspond to the central core 30 depicted in FIG. 4 (which does not contain any flow channels).

A flow-dispersion section 24 has a double-walled funnel shape, opening outwardly from the system inlet 20, toward the cylindrical section 32 that contains the liquid-flow channels 49. The double-wall construction of the flow-dispersion section 24 confines flow to between the inner and outer walls, e.g., along flow pathways 31.

As further illustrated in FIG. 4, the flow-dispersion section 24 of the system intersects the cylindrical, flow channel-containing section 32 of the system at a plane, and the inlet ends of the liquid-flow channels 49 are all located along this plane of intersection. As a result, except for the minor variation in flow length between flow along the radially inner wall of the flow-dispersion section 24 and flow along the radially outer wall of the flow-dispersion section 24, the lengths of all flow pathways 31 from the system inlet 20 to the entrances of the liquid-flow channels 49 will be the same. As in the above-described embodiments, this results in a more uniform pressure drop in the flow from system inlet 20 to the flow channel inlets circumferentially throughout the entire flow-dispersion section 24 of the system. This, in turn, reduces the variations in flow rates through the liquid-flow channels 49.

Figure 6:
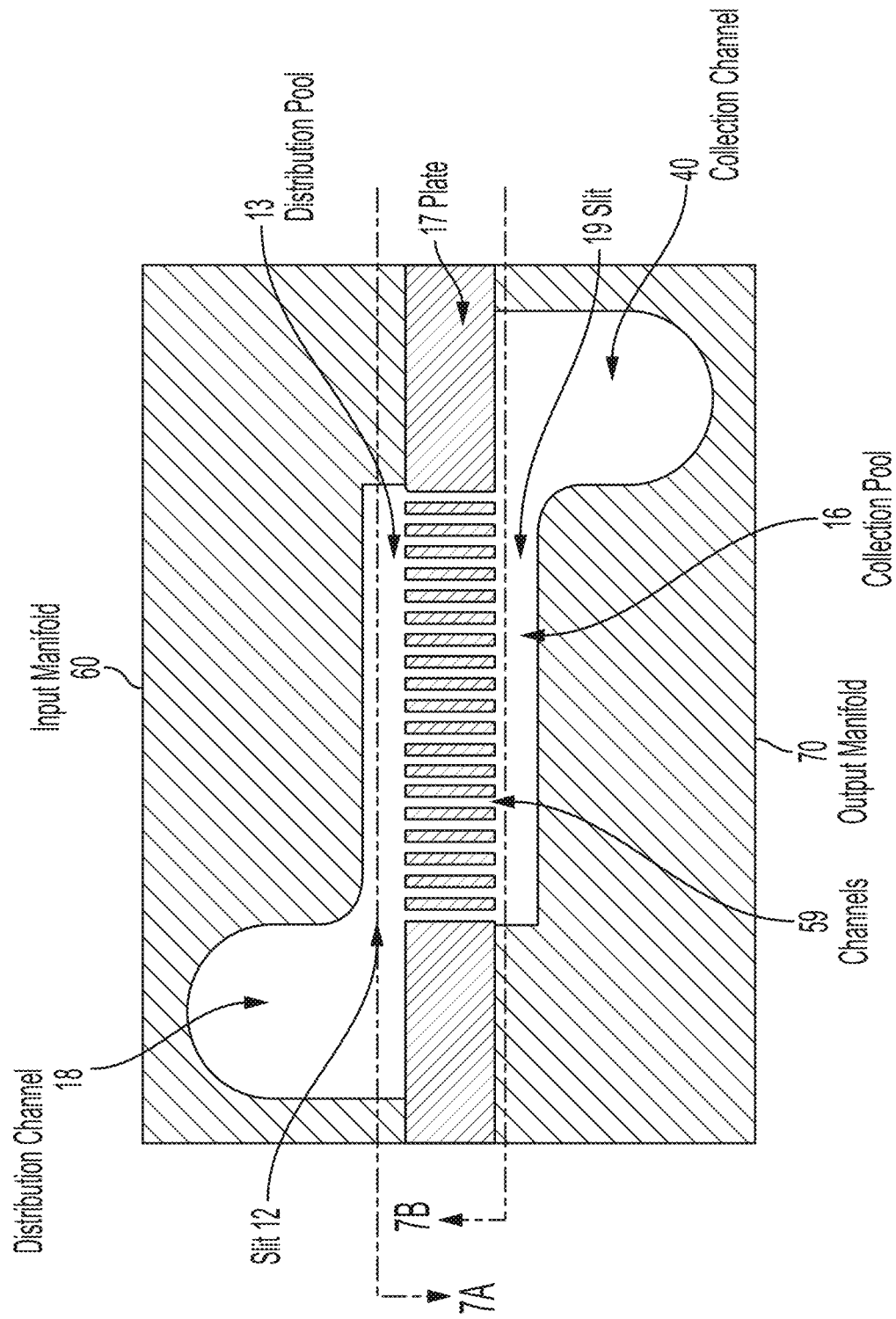
FIG. 6 is a cross-section of the FIG. 5 embodiment

FIGS. 5-7 depict another gas exchanger embodiment that reduces the variations in flow rates among the various liquid-flow channels in the system. In this embodiment, molecules are exchanged between a liquid and a gas, and this exchange occurs in one or more plates 17.

Each of the plates 17 may be formed from a very large number (e.g., millions or billions) of vertically aligned nanotubes positioned on a substrate, aligned similar to the way trees are vertically aligned in a forest or the way stalks of wheat are aligned in a field. A large number (e.g., thousands or hundreds of thousands) of preferably identical vertical liquid-flow channels pass through this forest/field of nanotubes, and these vertical liquid-flow channels can be analogized to clearings in the forest or unplanted regions in the field. The liquid-flow channels are wide enough for the relevant liquid to flow through in a vertical direction, and the nanotubes are spaced close enough together to retain the liquid within the liquid-flow channels. An opening in the substrate is provided beneath each of the liquid-flow channels. Examples of this variety of plate are described in U.S. Pat. No. 9,138,522, which is incorporated herein by reference in its entirety.

Alternatively, each of the plates 17 may be formed from a very large number (e.g., millions or billions) of interconnected vertically aligned nanotubes, with interconnections between the nanotubes that are sufficient to hold the plate together without requiring a substrate (in which case the substrate on which the nanotubes are originally grown can be removed). Examples of this variety of plate are described in "c-VACNT™ Enabled Fluid Reactor Innovations" by K. Strobl et al. (June 2019); "Vertically aligned carbon nanotube arrays as a thermal interface material" by L. Ping et al., APL Mater. 7, 020902 (2019); doi: 10.1063/1.5083868 (February 2019); and in "Transfer of vertically aligned carbon nanotube arrays onto flexible substrates for gecko-inspired dry adhesive application" by Yang Li et al., RSC Advances, Issue 58 (May 2015). As in the previous variation, when this variation of gas-exchange plate is used, a large number (e.g., thousands or hundreds of thousands) of preferably identical vertical liquid-flow channels pass through the forest of nanotubes. And here again, the liquid-flow channels are wide enough for the relevant liquid to flow through in a vertical direction, and the nanotubes are spaced close enough together to retain the liquid within the liquid-flow channels.

Whichever variety of plate 17 is used, the liquid will flow vertically through the vertical liquid-flow channels, while the gas that will exchange molecules with the liquid permeates the spaces between the nanotubes (analogous to the way air permeates through a forest of trees). Because the nanotubes in the field/forest are densely packed, they can present significant resistance to horizontal flow of gas. So to ensure that the gas reaches the liquid-flow channels, conduits that are free of nanotubes may optionally be included in the plate 17 in some embodiments. In these embodiments, gas will permeate to the boundaries of the liquid-flow channels by the combination of gas flowing through the conduits and diffusion from the conduits to nearby liquid-flow channels.

As explained in U.S. Pat. No. 9,138,522, nanotube-based gas exchange plates are particularly well-suited for oxygenating blood. In this situation, the liquid-flow channels that pass through the plate 17 should be sufficiently wide (e.g., between 2 and 500 µm) so that all the components of blood (including platelets, red blood cells, and white blood cells) can fit through the liquid-flow channels, and the nanotubes are spaced close enough to retain the plasma within the liquid-flow channels.

A multiplicity (e.g., thousands or hundreds of thousands) of liquid-flow channels 59 pass vertically through the plate 17, and the plate 17 is "sandwiched" between a plate-shaped input manifold 60 and a plate-shaped output manifold 70 (as best seen in FIGS. 5 and 6).

As illustrated in FIG. 6, the input manifold 60 and the output manifold 70 each have a cavity-forming recessed portion, which form a distribution pool plenum 13 on the upstream side of liquid-flow channels 59 and a collection pool plenum 16 on the downstream side of the liquid-flow channels 59, respectively.

Figure 7A:
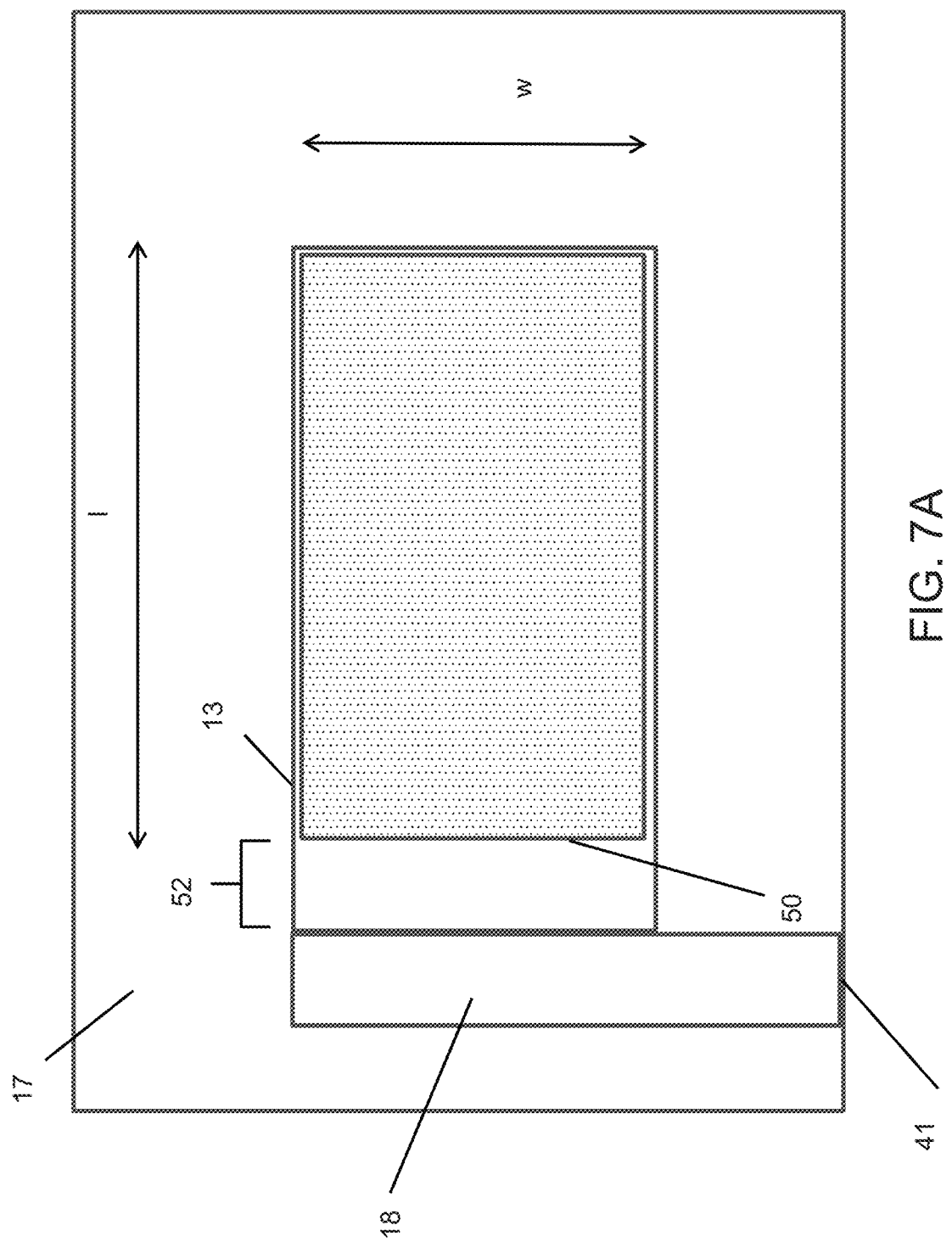
FIG. 7A is a schematic view of the FIG. 6 embodiment looking down from above the dashed line labeled 7A in FIG. 6.
Figure 7B:
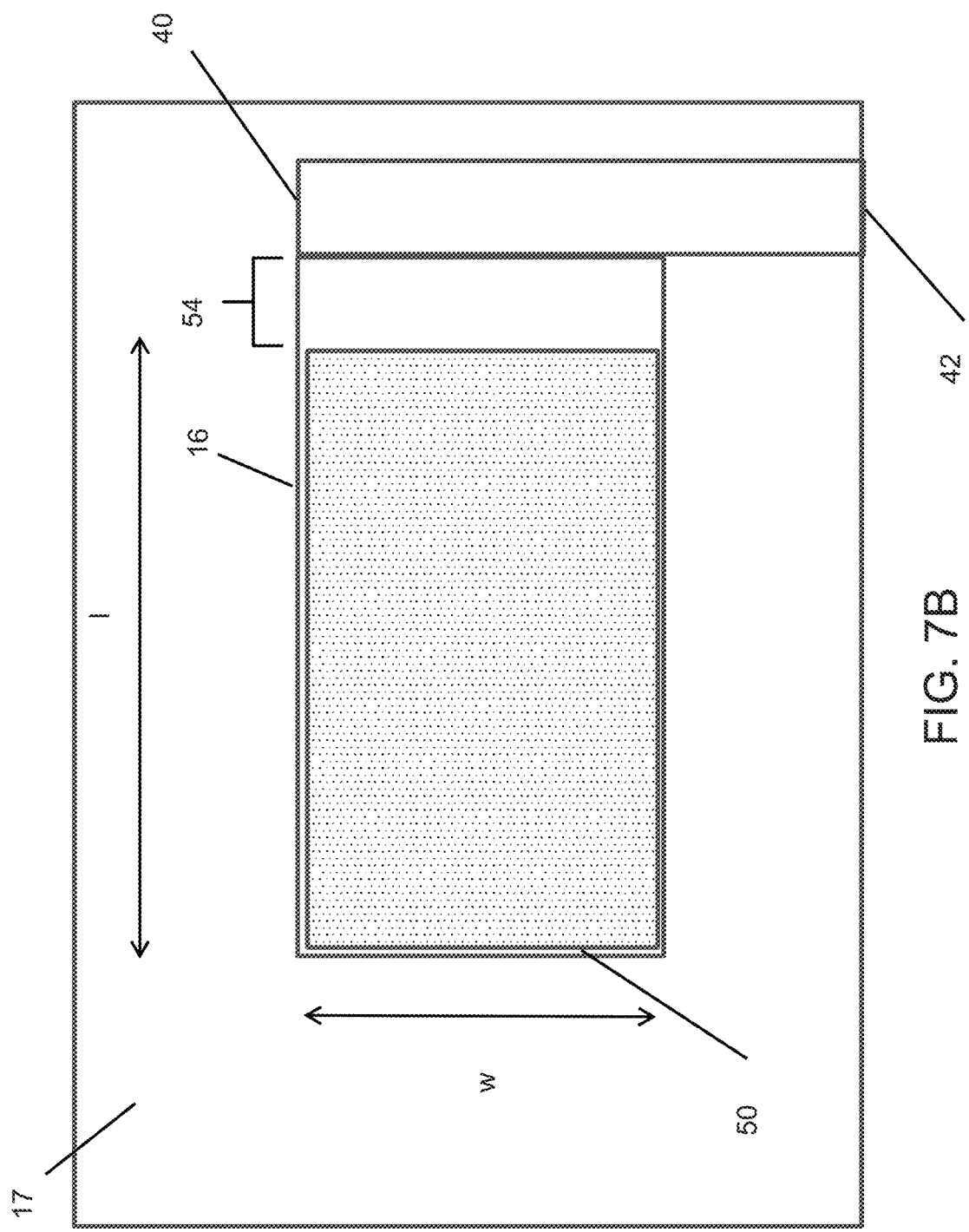
FIG. 7B is a schematic view of the FIG. 6 embodiment looking up from beneath the dashed line labeled 7B in FIG. 6.

FIGS. 7A and 7B are schematic representations of cross-sections of the FIG. 6 view, looking down from above the dashed line labeled 7A and looking up from beneath the dashed line labeled 7B, respectively. The portion of the plate 17 that liquid flows through is referred to herein as the transit region 50. This transit region 50 includes a large number (e.g., thousands or hundreds of thousands) of vertically oriented liquid-flow channels 59. In some embodiments, all of the channels that pass through the plate 17 are positioned within the transit region 50. In alternative embodiments, additional channels (not shown) pass through plate 17 are positioned outside the transit region 50, but liquid does not flow through those additional channels due to the positioning of other components within the system (e.g. the distribution pool plenum 13 and the collection pool plenum 16).

The transit region 50 has a length l and width w. The liquid-flow channels 59 within the transit region 50 are perpendicular to the surface of the plate 17. The density of the liquid-flow channels 59 will depend on the nature of the liquid-flow channels. For example, in a blood oxygenator implemented using a field of nanotubes with voids in those fields, liquid-flow channels with diameters between 2 and 500 µm may be used, and those channels may be spaced on centers between 10 and 2500 µm.

Note that in nanotube-based embodiments, when polar liquids (hydrophilic) such as aqueous solutions pass through the liquid-flow channels, the nanotubes are preferably left in their native hydrophobic state to prevent liquid escaping from the channels. In this situation, liquid containment within the channel is aided by the hydrophobicity of the nanotubes and the liquid (water) surface tension. In alternative embodiments, when non-polar liquids (hydrophobic) such as oil pass through those channels, it is preferable to incorporate modifications that make the boundary of the liquid-flow channels hydrophobic.

The distribution pool plenum 13 and collection pool plenum 16 are either as wide or wider than the transit region 50. Additionally, the distribution pool plenum 13 and the collection pool plenum 16 are each at least as long as the transit region 50. In some embodiments, the distribution pool plenum 13 and the collection pool plenum 16 are each significantly longer than the transit region 50 so as to form a distribution pool plenum feeder portion 52 that is located upstream of the transit region 50, as best seen in FIG. 7A, and a collection pool plenum run-out portion 54 that is located downstream of the transit region 50, as best seen in FIG. 7B.

As best seen in FIGS. 5 and 6, the system inlet is formed as an elongated, distribution channel 18 that is formed in the input manifold 60 at a location upstream of the distribution pool plenum 13, extending in the widthwise direction of the system, i.e., extending along the width direction of the transit region 50 (see FIG. 7A). Similarly, the system outlet is formed as an elongated, liquid collection channel 40 that is formed in the output manifold 70 at a location downstream of the collection pool plenum 16, extending in the widthwise direction of the system (see FIG. 7B). In some embodiments, both the distribution channel 18 and the liquid collection channel 40 are tubular in shape.

A liquid delivery opening 12 (which, in the illustrated embodiment, is generally slit-shaped) extends along the length of the distribution channel 18 and is positioned on the wall of channel 18 so as to deliver liquid to the distribution pool plenum 13 across the entire width of the distribution pool plenum 13. The liquid delivery opening 12 may empty directly into the distribution pool plenum 13, as depicted in FIG. 6, or it may empty into the distribution pool plenum feeder portion 52 in cases where such a feeder portion is provided. Similarly, a liquid collection opening 19 (which, in the illustrated embodiment, is also generally slit-shaped) extends along the length of the liquid collection channel 40 and is positioned on the wall of channel 40 so as to receive liquid from the collection pool plenum 16 from across the entire width of the collection pool plenum 16. The liquid collection opening 19 may receive liquid directly from the collection pool plenum 16, as depicted in FIG. 6, or it may receive liquid from the collection pool plenum run-out portion 54 in cases where such a run-out portion is provided.

As best seen in FIG. 5, liquid (e.g., blood) enters at inlet port 41 at the front left corner of the system and flows into the distribution channel 18. It then exits the distribution channel 18 through liquid delivery opening 12. The liquid that exits the liquid delivery opening 12 will flow towards the right. This flow will have a planar shape, and the presence of the optional distribution pool plenum feeder portion 52 (if it is provided) will, in particular, help distribute the flow to the right and allow it to become uniform before it reaches the leading edge of the transit region 50. In some embodiments, the liquid delivery opening 12 is shaped such that its resistance to flow through it will compensate for the pressure drop along the distribution channel 18 so as to maintain uniform flow. For example, the liquid delivery opening 12 may be wider at the downstream end of the distribution channel 18 than at the upstream end so as to present less resistance to flow at the downstream end (where pressure along the distribution channel 18 will be lower); this allows flow to pass out of the distribution channel at essentially the same rate along the length of the distribution channel 18.

Liquid will then fill the distribution pool plenum 13, which may have a constant height so as to provide a completely cuboid volume. In alternative embodiments (not shown), the roof of the distribution pool plenum 13 is sloped. The liquid in the distribution pool plenum 13 will then flow vertically through the liquid-flow channels 59 that pass through the plate 17 into the collection pool plenum 16.

Meanwhile, while the liquid is passing vertically through the liquid-flow channels 59 in the plate 17 as explained above, a gas (e.g., air, oxygen, etc.) permeates perpendicular to the vertical direction in portions of the plate that are outside the liquid-flow channels so that exchange of molecules between the blood and the gas can occur at the boundary of the liquid-flow channels.

The gas is provided to the portions of the plate that are outside the liquid-flow channels by at least one gas port disposed in fluid communication with those portions. In some embodiments, the at least one gas port comprises a first gas port configured to supply the gas to the portions of the plate that are outside the liquid-flow channels, and a second gas port configured to vent the gas from the portions of the plate that are outside the liquid-flow channels. As noted above, the gas will permeate the space between the nanotubes and reach the boundary of the liquid-flow channels by flow and/or diffusion.

As the liquid passes through the liquid-flow channels 59 in the plate 17, the gas that permeates the portions of the plate that are outside the liquid-flow channels will come into contact with the liquid in the liquid-flow channels 59, so that an exchange of molecules can occur between the liquid and the gas. For example, when the liquid in the liquid flow channels 59 is blood in the gas in the portions of the plate 17 that are outside the liquid-flow channels is oxygen, oxygen will enter the blood from the gas and carbon dioxide will exit the blood into the gas. Examples of this type of exchange of gases between a liquid in liquid-flow channels and a gas surrounding those channels include the examples described in U.S. Pat. No. 9,138,522.

After flowing through the liquid-flow channels 59 in the plate 17, the liquid will fill the collection pool plenum 16. Like the distribution pool plenum 13, the collection pool plenum 16 may have a constant height so as to provide a completely cuboid volume. In alternative embodiments (not shown), the floor of the collection pool plenum 16 is sloped. From the collection pool plenum 16, liquid flows through the liquid collection opening 19 and into the liquid collection channel 40, passing first through the collection pool plenum run-out portion 54 if one is present. Like the distribution pool plenum feeder portion 52, the optional collection pool plenum run-out portion 54, if present, will help maintain uniformity of flow through the system as it moves past the trailing edge of the transit region 50 and into the liquid collection opening 19 of the liquid collection channel 40. Furthermore, like the liquid delivery opening 12, the liquid collection opening 19 may be shaped such that its resistance to flow through it will compensate for the pressure drop along the liquid collection channel 40 so as to maintain uniform flow. Liquid then exits the system at outlet port 42, which is located opposite to the inlet port 41 in that it is located on the opposite side of the system as well as at the opposite end of the system from inlet port 41.

Figure 8:
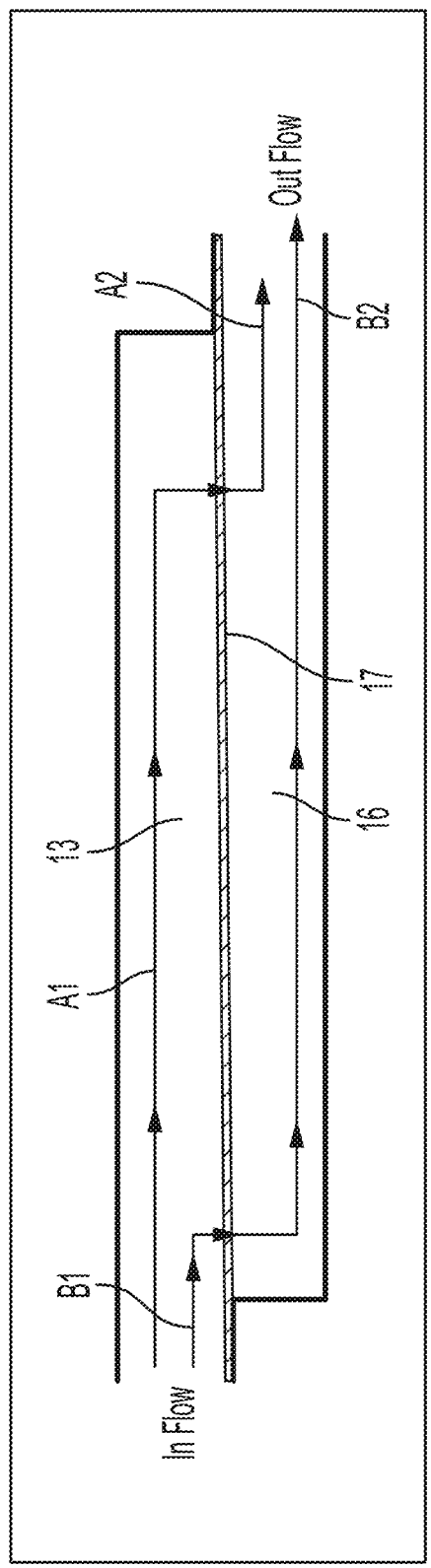
FIG. 8 is a schematic representation of two different flow paths through the FIG. 5-7 embodiment.

The flow paths of the liquid in the FIGS. 5-7 embodiment is illustrated in FIG. 8. As illustrated, liquid (for example low oxygen blood) enters the system and fills the distribution pool plenum 13. The liquid then passes through the liquid-flow channels 59 in the plate 17 (where gas exchange occurs). Next, the liquid fills and flows along collection pool plenum 16 and is eventually collected in collection channel 40 and exits the system at outlet port 42.

In FIG. 8, two exemplary flow pathways from the distribution pool plenum 13 to the collection pool plenum 16 that traverse through the transit region 50 are depicted. The first path A1/A2 passes through the transit region 50 at a location that is close to the upstream edge of the transit region 50, and the second path B1/B2 passes through the transit region at a location that is close to the downstream edge of the transit region 50. The total flow resistance along the first flow path is represented by A1+A2, while the total flow resistance along the second flow pathway is represented by B1+B2. Notably, the sum of the lengths of pathways A1 and A2 is the same as the sum of the lengths of pathways B1 and B2. And similarly, the total distance traveled for each and every flow pathway through the system will be the same. Thus, the pressure differences driving all flows will be more uniform throughout the system, as will be the associated flow rates.

Figure 9:
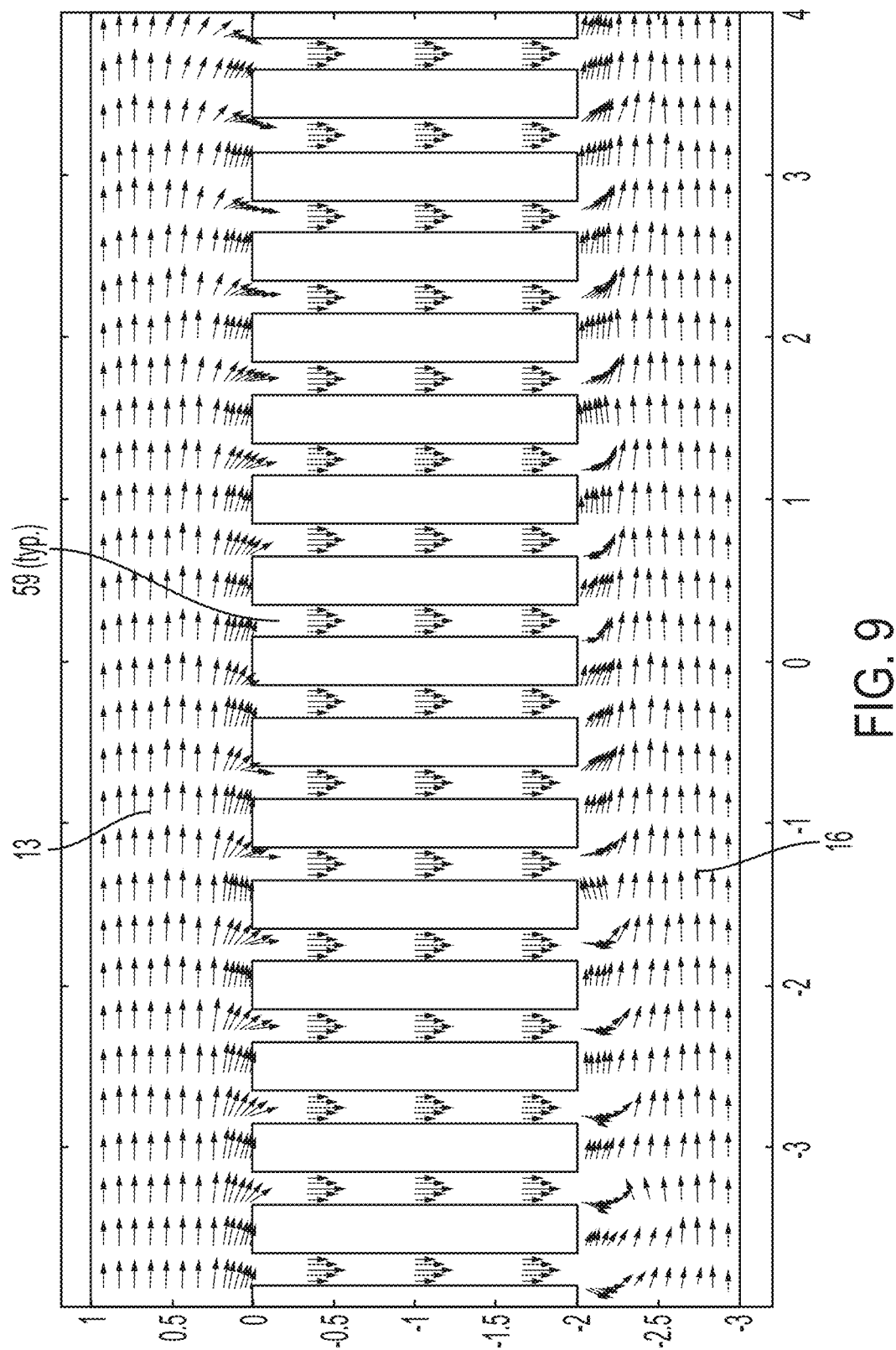
FIG. 9 depicts simulated flow patterns through the FIG. 5-7 embodiment.

FIG. 9 depicts simulated flow patterns through a cross section of the FIGS. 5-7 embodiment that passes from the distribution pool plenum 13 to the collection pool plenum 16 through a plurality of liquid-flow channels 59 in a plate 17.

In this figure, the length of each arrow represents the flow velocity at the corresponding point. As shown in FIG. 9, the flow velocities in the channels are very similar. Projected deviations from uniform flow are dependent on the liquid properties and the dimensions of the different components of the system. Sample deviations were calculated and are presented (in % deviation from the average flow) in FIGS. 10 and 11 for two examples of different values of the resistance to flow of a one-square-centimeter plate 17 containing a large number of liquid-flow channels 59 passing through it.

Figure 10:
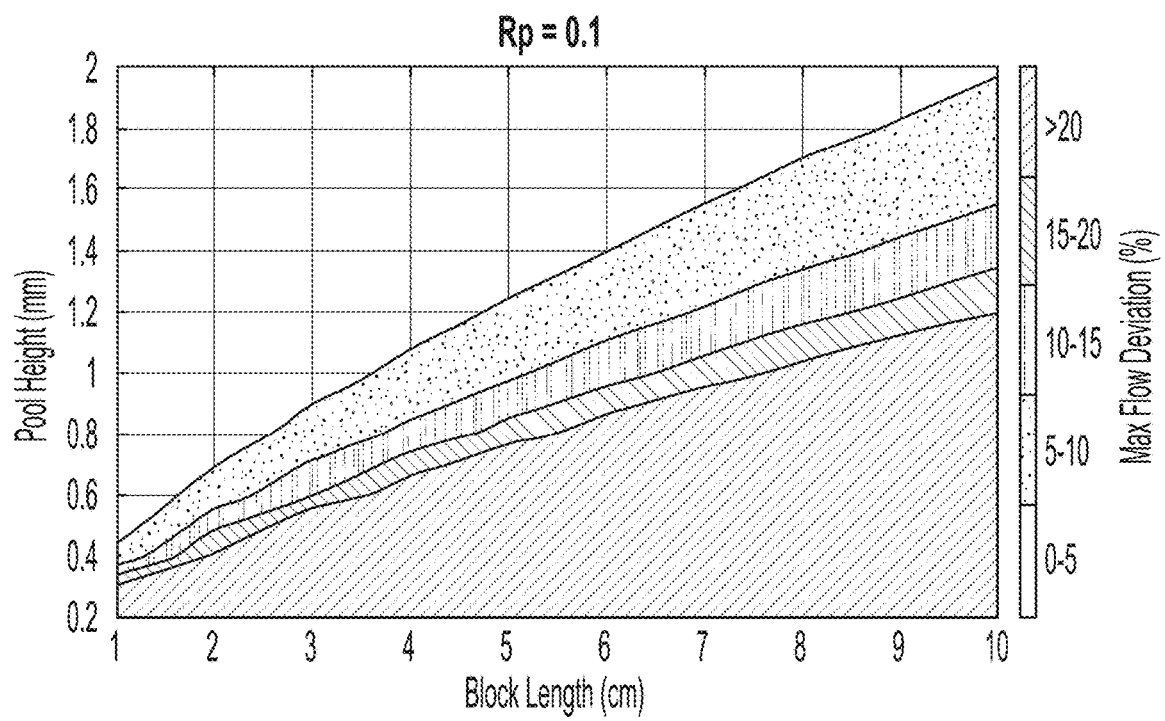
FIGS. 10 and 11 are graphs illustrating flow deviation for the FIG. 5-7 embodiment.
Figure 11:
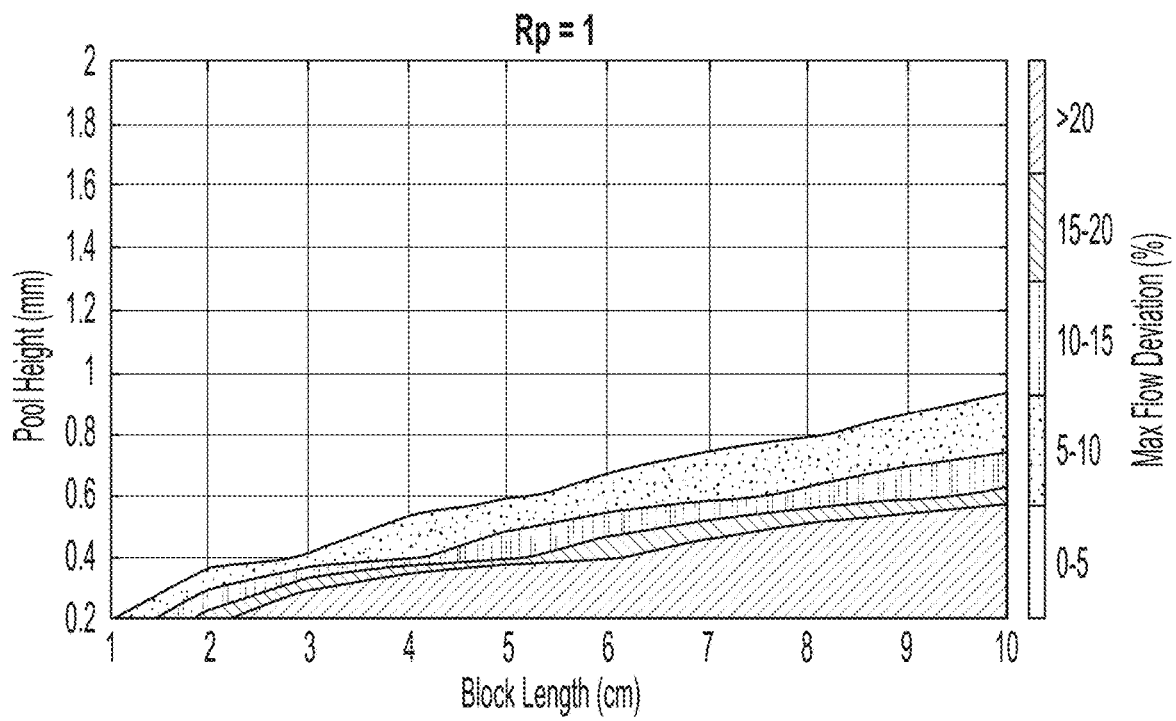

In the case of FIG. 10, the relevant parameters were as follows:
RP=0.1 (mmHg/ml/min per cm$^2$)
Channel length—1 mm
Channel diameter—100 µm
Distance between Channels—150 µm
No. of channels in 1 cm$^2$ area—1600
Configuration—Cubic Grid Type And in the case of FIG. 11, the relevant parameters were as follows:
RP=1 (mmHg/ml/min per cm$^2$)
Channel length—1 mm
Channel diameter—20 µm
Distance between Channels—30 µm
No. of channels in 1 cm$^2$ area—111,111
Configuration—Cubic Grid Type In both cases, the deviation of flow rate between the various fluid-flow channels in the system is relatively low.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A distributed-flow liquid flow system, comprising:
    a gas-exchange plate having an upstream side and a downstream side, the gas-exchange plate having a transit region that includes at least 1000 liquid-flow channels extending through the gas-exchange plate in a first direction from the upstream side of the gas-exchange plate to the downstream side of the gas-exchange plate, the transit region having a length and a width, wherein the gas-exchange plate is configured so that a gas can permeate portions of the gas-exchange plate that are outside the at least 1000 liquid-flow channels;
    a distribution pool plenum located on the upstream side of the gas-exchange plate adjacent to the transit region, wherein the distribution pool plenum is shaped and dimensioned to convey the liquid to the entire upstream side of the transit region, wherein the distribution pool plenum is at least as wide as the transit region;
    a collection pool plenum located on the downstream side of the gas-exchange plate adjacent to the transit region, wherein the collection pool plenum is shaped and dimensioned to receive liquid that has transited the transit region, wherein the collection pool plenum is at least as wide as the transit region;
    a liquid distribution channel located upstream of the distribution pool plenum, the liquid distribution channel having an elongated liquid delivery opening that extends across the width direction of the transit region, wherein the elongated liquid delivery opening is positioned to deliver liquid to the distribution pool plenum;
    a liquid collection channel located downstream of the collection pool plenum, the liquid collection channel having an elongated liquid collection opening that extends across the width direction of the transit region, wherein the elongated liquid collection opening is positioned to receive liquid from the collection pool plenum;
    a liquid input port disposed in fluid communication with the liquid distribution channel;
    a liquid output port disposed in fluid communication with the liquid collection channel; and
    at least one gas port disposed in fluid communication with the portions of the gas-exchange plate that are outside the at least 1000 liquid-flow channels.

2. The distributed-flow liquid flow system of claim 1, wherein the liquid distribution channel is positioned sufficiently upstream of the distribution pool plenum to form a distribution pool plenum feeder portion extending from the elongated liquid delivery opening to a leading edge of the distribution pool plenum, over which distribution pool plenum feeder portion the flow of liquid exiting from the elongated liquid delivery opening becomes essentially uniform before entering the distribution pool plenum.

3. The distributed-flow liquid flow system of claim 1, wherein the liquid collection channel is positioned sufficiently downstream of the collection pool plenum to form a collection pool plenum run-out portion extending from a trailing edge of the collection pool plenum to the elongated liquid collection opening so as to maintain essentially uniform flow of liquid as it exits the collection pool plenum.

4. The distributed-flow liquid flow system of claim 1, wherein the elongated liquid delivery opening has a width that varies along the length of the liquid distribution channel, from a liquid entry location to a distal end, so as to maintain uniform velocity of liquid exiting the liquid distribution channel along the length of the liquid distribution channel.

5. The distributed-flow liquid flow system of claim 1, wherein the elongated liquid collection opening has a width that varies along the length of the liquid collection channel, from a distal end to a liquid exit location, so as to maintain uniform velocity of liquid entering the liquid collection channel along the length of the liquid collection channel.

6. The distributed-flow liquid flow system of claim 1, wherein the liquid distribution channel has a liquid inlet and the liquid collection channel has a liquid outlet and the liquid inlet and liquid outlet are located on opposite sides of the transit region in both widthwise and lengthwise directions.

7. The distributed-flow liquid flow system of claim 1, wherein a liquid in the distributed-flow liquid flow system is blood and the gas comprises air.

8. The distributed-flow liquid flow system of claim 1, wherein a liquid in the distributed-flow liquid flow system is blood and the gas comprises oxygen.

9. The distributed-flow liquid flow system of claim 1, wherein the gas-exchange plate comprises a field of at least one million vertically oriented nanotubes, wherein the at least 1000 liquid-flow channels comprise vertical voids within the fields, the voids having diameters between 2 and 500 µm, wherein the at least one million vertically oriented nanotubes are positioned close enough together to retain the liquid within the voids, and wherein the at least one million vertically oriented nanotubes are positioned far enough apart so that gas can reach the at least 1000 liquid-flow channels.

10. The distributed-flow liquid flow system of claim 1, wherein the at least one gas port comprises an input gas port configured to supply the gas to the portions of the gas-exchange plate that are outside the at least 1000 liquid-flow channels, and an output gas port configured to vent the gas from the portions of the gas-exchange plate that are outside the at least 1000 liquid-flow channels.

11. The distributed-flow liquid flow system of claim 1, wherein the distribution pool plenum has a constant height.

12. The distributed-flow liquid flow system of claim 11, wherein the collection pool plenum has a constant height.

13. The distributed-flow liquid flow system of claim 1, wherein the distribution pool plenum has a sloped roof.

* * * * *